(12) United States Patent
Cho

(10) Patent No.: US 8,166,772 B2
(45) Date of Patent: May 1, 2012

(54) FLEXILE PLATED COOLING PACK OF HEADWEAR AND METHOD FOR MAKING THE SAME

(75) Inventor: Byoung-Woo Cho, Gyeonggi-do (KR)

(73) Assignee: Yupoong, Inc. (KR)

( * ) Notice: Subject to any disclaimer, the term of this patent is extended or adjusted under 35 U.S.C. 154(b) by 876 days.

(21) Appl. No.: 12/246,541

(22) Filed: Oct. 7, 2008

(65) Prior Publication Data

US 2010/0083421 A1   Apr. 8, 2010

Related U.S. Application Data

(63) Continuation-in-part of application No. 29/303,435, filed on Feb. 8, 2008, now Pat. No. Des. 592,836, and a continuation-in-part of application No. 29/303,417, filed on Feb. 8, 2008, now Pat. No. Des. 609,884.

(51) Int. Cl.
   *F25D 23/12* (2006.01)
(52) U.S. Cl. ....................................................... 62/259.3
(58) Field of Classification Search ................. 62/259.3, 62/530
   See application file for complete search history.

(56) References Cited

U.S. PATENT DOCUMENTS

| | | | |
|---|---|---|---|
| 418,282 A | 12/1889 | Fechter | |
| 748,634 A | 1/1904 | Murphy | |
| D91,881 S | 4/1934 | Herrel | |
| D203,071 S | 11/1965 | Harty | |
| 4,237,558 A | 12/1980 | Mackenroth, III et al. | |
| 4,270,229 A | 6/1981 | Lipschutz | |
| 4,312,076 A | 1/1982 | Gamm | |
| 4,484,363 A * | 11/1984 | Varanese | 2/209.13 |
| 4,854,319 A * | 8/1989 | Tobin | 607/109 |
| D343,282 S | 1/1994 | Irish | |
| D345,644 S | 4/1994 | Harvie | |
| 5,327,585 A * | 7/1994 | Karlan | 2/7 |
| 5,348,510 A | 9/1994 | DuPont et al. | |
| 5,365,607 A * | 11/1994 | Benevento et al. | 2/181.4 |
| 5,373,586 A | 12/1994 | Brosnan | |
| 5,385,770 A | 1/1995 | Julnes | |
| D375,844 S | 11/1996 | Edwards et al. | |

(Continued)

OTHER PUBLICATIONS

U.S. Appl. No. 29/303,417 by Byoung-Woo Cho, "Gore-Shaped Cooling Pack"; filed Feb. 8, 2008 (Pending).

(Continued)

*Primary Examiner* — Melvin Jones
(74) *Attorney, Agent, or Firm* — Fellers, Snider, Blankenship, Bailey & Tippens, P.C.

(57) ABSTRACT

The present invention relates to a flexible plated cooling pack for headwear and a method for making the same that is capable of providing a sufficient cooling effect with a small amount of coolant, not causing worry about leakage of the coolant, and providing a cushion effect without a volume variance regardless of many uses, as well as the cooling effect.

The flexible plated cooling pack has an inner and outer synthetic resin film sheet bonded each other and a coolant filled therein, wherein the outer synthetic resin film sheet has a shape respectively corresponding to a piece of the crown portion and a sweatband and the coolant is always maintained in at least a gel state. The flexible plated cooling pack may be disposed in an inner portion of the crown portion and the sweatband of the headwear or may be inserted in a pocket formed at an inner portion of the crown portion and the sweatband of the headwear.

16 Claims, 7 Drawing Sheets

U.S. PATENT DOCUMENTS

| | | |
|---|---|---|
| 5,887,284 A | 3/1999 | Simmons |
| 5,907,871 A | 6/1999 | Austin |
| 5,956,759 A | 9/1999 | Benedict |
| D421,198 S | 2/2000 | Surface |
| D422,151 S | 4/2000 | Hwang et al. |
| D428,267 S | 7/2000 | Romano et al. |
| D428,710 S | 8/2000 | Romano et al. |
| 6,108,818 A | 8/2000 | Eisenberg |
| D431,369 S | 10/2000 | Thomas |
| D456,533 S | 4/2002 | Moller, Jr. |
| 6,477,715 B2 | 11/2002 | Shin |
| D466,702 S | 12/2002 | Carlson et al. |
| D496,145 S | 9/2004 | Lacey |
| 6,792,624 B2 | 9/2004 | Simmons |
| 6,857,134 B1 | 2/2005 | Cowell |
| 6,904,617 B2 * | 6/2005 | Tsai ............ 2/209.13 |
| 6,918,139 B2 | 7/2005 | Okot |
| 7,010,814 B2 | 3/2006 | Benziger |
| 7,020,900 B2 | 4/2006 | Ngan |
| 7,043,767 B2 | 5/2006 | Jaeger |
| D526,128 S | 8/2006 | Delaney |
| 7,127,907 B2 * | 10/2006 | Tu ............ 62/259.3 |
| D538,514 S | 3/2007 | Nadeau |
| D540,095 S | 4/2007 | Lee |
| 7,278,173 B2 | 10/2007 | Turner |
| D572,068 S | 7/2008 | Lin |
| D592,836 S | 5/2009 | Cho |
| D609,884 S | 2/2010 | Cho |
| 2005/0235396 A1 | 10/2005 | Lee |
| 2007/0077223 A1 | 4/2007 | Tai |
| 2007/0079424 A1 | 4/2007 | Cho |
| 2007/0143906 A1 | 6/2007 | Renteria |
| 2007/0245456 A1 | 10/2007 | Cho |

OTHER PUBLICATIONS

U.S. Appl. No. 29/303,435 by Byoung-Woo Cho, "Band-Shaped Cooling Pack"; filed Feb. 8, 2008 (Pending).

* cited by examiner

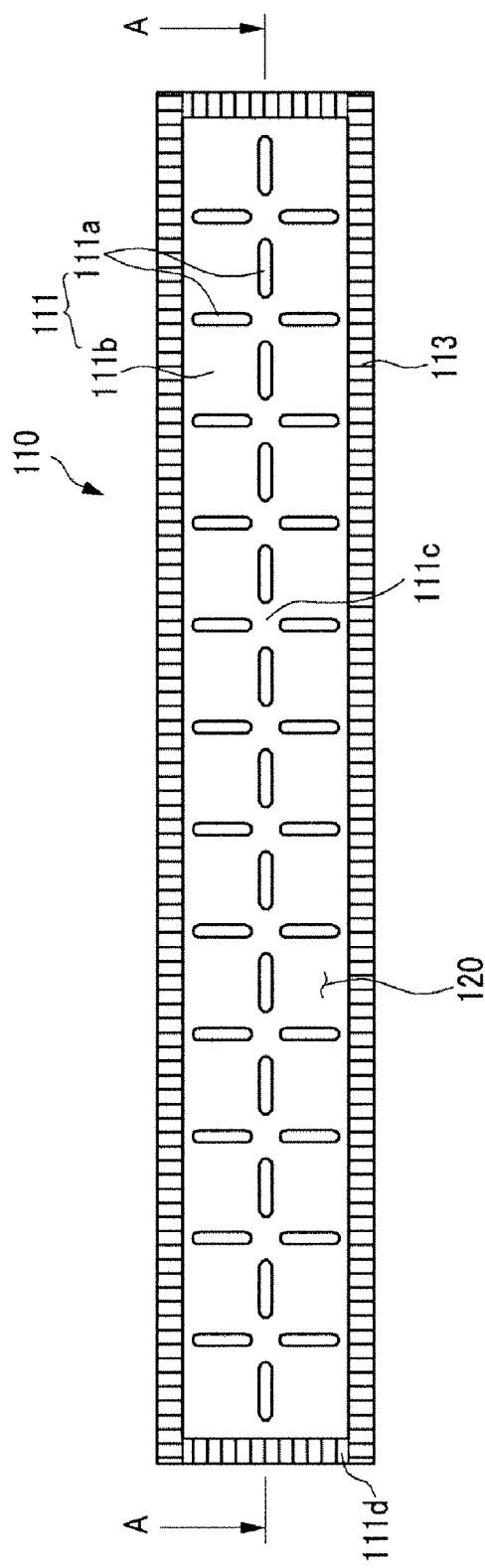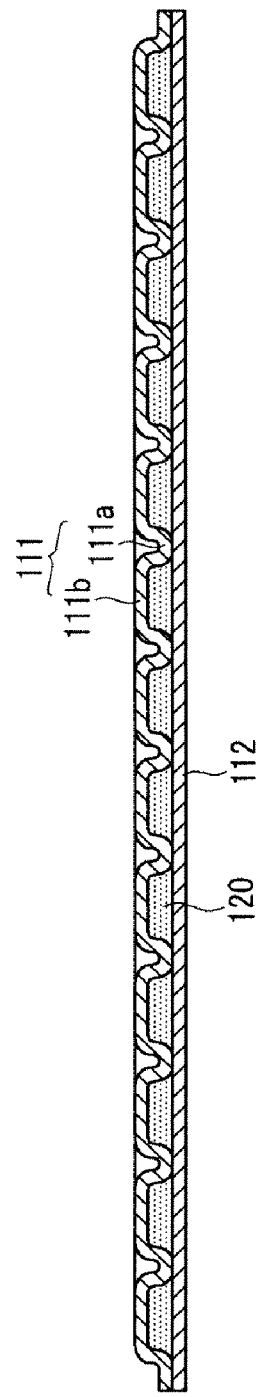

FLEXILE PLATED COOLING PACK OF HEADWEAR AND METHOD FOR MAKING THE SAME

CROSS REFERENCE TO RELATED APPLICATION

This application is a continuation-in-part of both U.S. Design patent application Ser. No. 29/303,435 entitled BAND-SHAPED COOLING PACK filed Feb. 8, 2008 now U.S. Pat. No. Des. 592,836, and U.S. Design patent application Ser. No. 29/303,417 entitled GORE-SHAPED COOLING PACK filed Feb. 8, 2008 now U.S. Pat. No. Des. 609,884.

BACKGROUND OF THE INVENTION

1. Field of the Invention

The present invention relates to a flexible plated cooling pack for headwear, and a method for making the same. More particularly, the present invention relates to a flexible plated cooling pack for headwear and a method for making the same that is capable of providing a sufficient cooling effect with a small amount of coolant, without worry regarding leakage of the coolant, and that provides a cushion effect without a volume variance as well as the cooling effect.

2. Description of the Related Art

Generally, headwear includes a crown portion that is placed on a wearer's head and a visor portion protruding entirely or partially outward from the crown portion.

Such headwear may prevent the face from being burned and the head and the like from being heated by direct rays of the sun or ultraviolet rays during hot weather such as the summer season, and may prevent the eyes from being exposed by the direct rays of the sun, thus it may be widely used generally or for sports.

In addition, such headwear may prevent the head from being affected by cool weather because it is made of an insulating fabric, so that it may prevent a loss of heat.

However, if the headwear is worn for a long time when the sunlight is strong and the temperature is high, the headwear may interrupt heat or sweat dissipation, and thus the sweat may build up or the head may be heated to a high temperature.

For the purpose of solving such a problem, an ice pack filled with a coolant or refrigerant such as air or water is disposed thereto.

However, such a coolant or refrigerant has a problem in that it may have the cooling effect for a relatively short time. Also, the coolant may easily leak though the ice pack and accordingly the leaked coolant may contaminate the headwear or the surroundings thereof. In addition, the coolant or refrigerant may be a solid because of a phase change and accordingly it may press the head painfully.

In addition, the ice pack must have a relative large capacity so as to provide a sufficient cooling effect and must be previously refrigerated. Thus, it is difficult to always carry or keep the same.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a flexible plated cooling pack for headwear and a method for making the same having advantages of providing a sufficient cooling effect with a small amount of coolant for a long time, being easily carried and kept, not causing worry about leakage of the coolant, and providing a cushion effect without a volume variance regardless of many uses so that the shape or design of the headwear may be maintained.

An exemplary embodiment of the present invention provides a flexible plated cooling pack for headwear having a crown portion that is placed on the head, a visor portion protruding outward from at least a part of the crown portion to shield sunlight, and a sweatband disposed according to a head circumferential direction at a lower portion of the crown portion, wherein the flexible plated cooling pack having a shape corresponding to a piece, the piece composing the crown portion so that it is disposed at an inner portion thereof and having a coolant filled therein such that the coolant is always maintained in at least a gel state.

According to an exemplary embodiment of the present invention, the flexible plated cooling pack may be fixed between a lower portion of the crown portion and the sweatband according to a head circumferential direction at a lower portion of the crown portion so that it may be easy to carry, keep, and replace the same.

In addition, according to an exemplary embodiment of the present invention, the flexible plated cooling pack has an outer panel and a coolant, which are not cooled to sub-zero temperatures so that the user may always feel a cushion effect and the flexible plated cooling pack may closely contact the shape of the crown portion, and it may not change the same.

In addition, according to an exemplary embodiment of the present invention, the flexible plated cooling pack has a plurality of lattices formed by high-frequency heating on the outer panel that has good elasticity and thermal transmission so that it may have sol filler uniformly that does not becomes thicker, and when it is pressed, the sol filling material may not easily leak such that it does not contaminate the head and surroundings thereof.

According to an exemplary embodiment of the present invention, the flexible plated cooling pack has a wide flange on the periphery portion thereof, which is formed by the high-frequency heating, so that it may prevent the filling material from leaking and allow the flexible plated cooling pack to be easily connected to each other.

BRIEF DESCRIPTION OF THE DRAWINGS

FIG. 2A and FIG. 2B are respectively a perspective view and a cross-sectional view of a flexible plated cooling pack disposed along a circumferential portion of a crown portion according to an exemplary embodiment of the present invention.

DETAILED DESCRIPTION OF THE EMBODIMENTS

Figure 1:
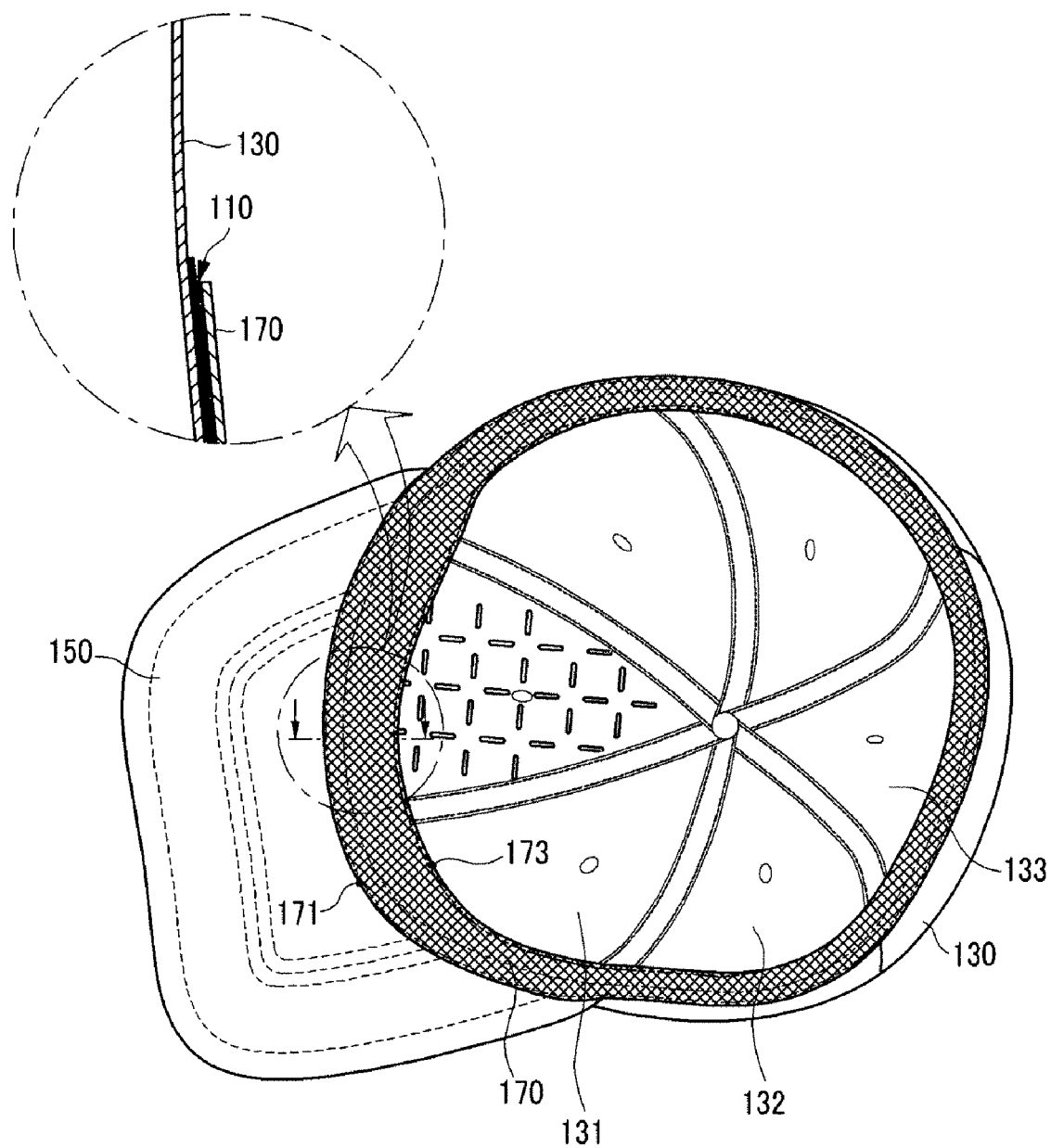
FIG. 1 is a perspective view of a flexible plated cooling pack in a state in which at least a portion thereof is inserted between a crown portion and a sweat band according to a first exemplary embodiment of the present invention.

A preferred exemplary embodiment of the present invention will be described with reference to attached drawings.

In the following detailed description, only certain exemplary embodiments of the present invention have been shown and described, simply by way of illustration.

As those skilled in the art would realize, the described embodiments may be modified in various different ways, all without departing from the spirit or scope of the present invention.

Accordingly, the drawings and description are to be regarded as illustrative in nature and not restrictive. Like reference numerals designate like elements throughout the specification.

According to an exemplary embodiment of the present invention, it is exemplified that the headwear is a golf cap, but it may be any item that may be worn on the head, such as a visor, a baseball cap, a sun cap, or another kind of hat.

A flexible plated cooling pack and headwear having the same according to the first exemplary embodiment of the present invention will be described with reference to FIG. 1 through FIG. 3B in detail.

FIG. 1 is a perspective view of a flexible plated cooling pack in a state in which at least a portion thereof is inserted between a crown portion and a sweat band according to an exemplary embodiment of the present invention.

Figure 3A:
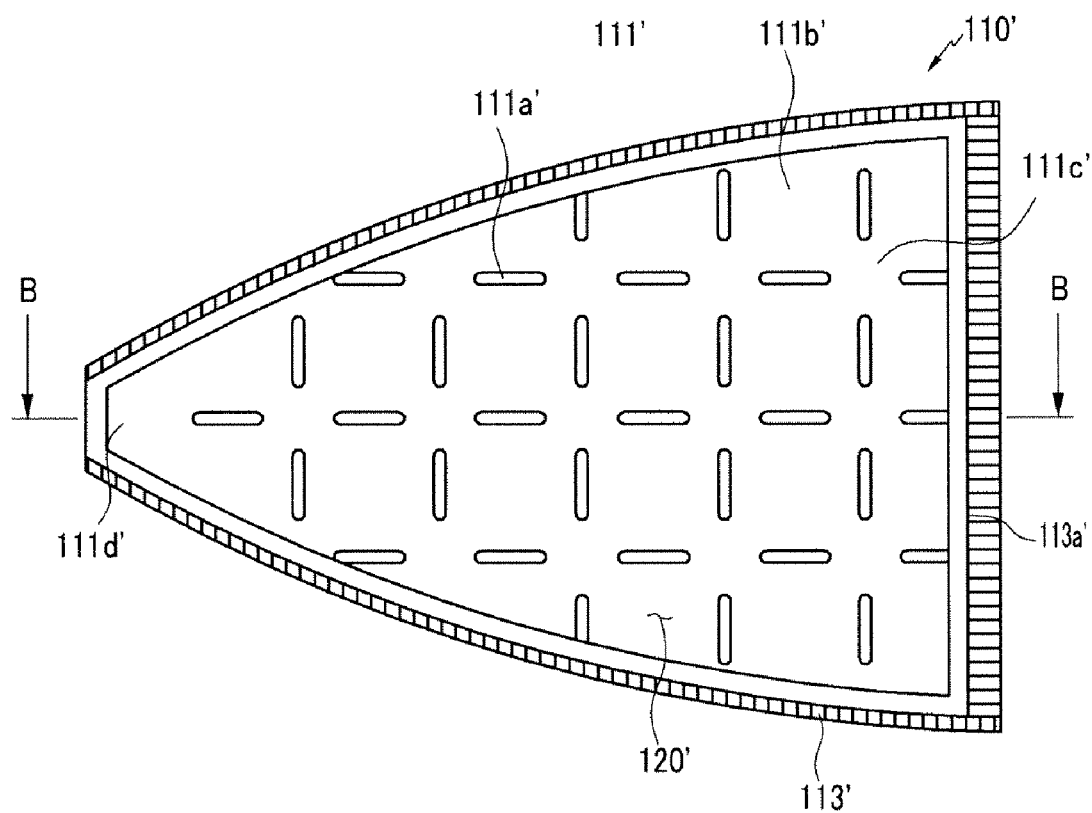
FIG. 3A and FIG. 3B are respectively a perspective view and a cross-sectional view of a flexible plated cooling pack disposed along a height direction of a crown portion according to an exemplary embodiment of the present invention.
Figure 3B:
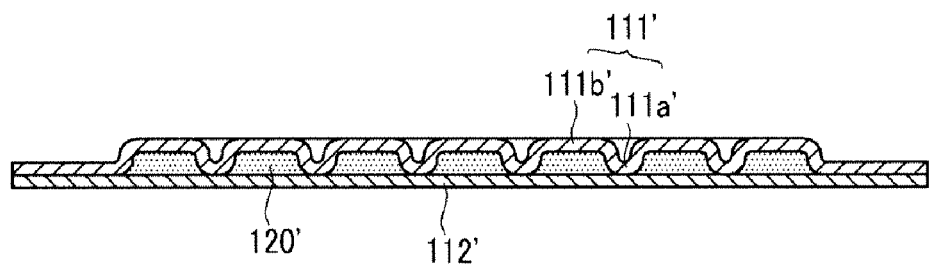

FIG. 2A and FIG. 2B are respectively a perspective view and a cross-sectional view of a flexible plated cooling pack disposed along a circumferential portion of a crown portion according to an exemplary embodiment of the present invention. FIG. 3A and FIG. 3B are respectively a perspective view and a cross-sectional view of a flexible plated cooling pack disposed along a height direction of a crown portion according to an exemplary embodiment of the present invention.

As shown in FIG. 1 to FIG. 3B, according to an exemplary embodiment of the present invention, headwear 100 may include a crown portion 130 that is placed on the head, a visor portion 150 protruding to shield sunlight at a part or the entirety of the lower portion of the crown portion 130, and a sweatband 170 having a fixed end portion 171 connected at the lower portion of the crown portion 130 and a free end portion 173 opposite thereto. The sweatband 170 may have elasticity.

When the sweatband 170 has elasticity, it may stretch along the circumferential portion of the crown portion 130 so that it may provide good wearing comfort when wearing it regardless of the size of the head. It may have a width of 1.5 to 7 cm.

Preferably, the sweatband 170 may be made from a monofilament fiber that makes it easier for the sweatband to maintain its original shape and guarantees free and comfortable movement due to its significant capacity to stretch and ability to spring back to its shape. The monofilament fiber may provide a softer, more natural feel and a more cotton-like characteristic when it is made from one of nylon, PET, polyethylene (PE), PP, or the like.

According to an exemplary embodiment of the present invention, the headwear 100 may include at least a part of a flexible plated cooling pack 110 between the crown portion 130 and the free end portion 173 of the sweatband 170.

When the flexible plated cooling pack 110 has a shape corresponding to the plurality of pieces 131, 132, and 133 of the crown portion 130 and the sweatband 150 disposed along the head circumferential direction of the crown portion 130, a plurality of flexible plated cooling packs 110 may be easily connected to form uniform headwear and to provide a uniform cooling effect for the entirety of the head, and also each of the flexible plated cooling packs 110 may provide an efficient cooling effect.

It is preferable for an outer synthetic resin film sheet 111 of the flexible plated cooling pack 110 to be made of a transparent and durable material such as thermoplastic polyurethane (TPU), so that it may be environmentally friendly, have good durability and elasticity, and may also have a freezing point of below −40° C. to provide a softer feel at sub-zero temperatures. In addition, it may have durability with respect to oil or fatty acids so that it may protect against leakage of oil or fatty acids stored therein.

However, the present invention is not limited thereto. Any product that is environmentally friendly, transparent, and does not freeze at sub-zero temperatures may be used as the outer synthetic resin film sheet. It may be, for example, one of thermoplastic polyurethane, polyethylene, and polyvinyl acetate films as shown in Table 1.

Table 1 shows what does not freeze at sub-zero temperatures and may be used as the outer synthetic resin film sheet.

TABLE 1

| TPU | Not freezing |
| High-density polyethylene (HDPE) | Freezing |
| Ethylene-vinyl-acetate (EVA) | Freezing |
| Ethylene-propylene-dyne copolymer (EPDM) | Freezing |
| Polyethylene film | Not freezing |
| Polyvinyl chloride | Not freezing |

FIG. 2A and FIG. 2B illustrate the flexible plated cooling pack 110 having a tape shape corresponding to the sweatband 150.

As shown FIG. 2A and FIG. 2B, it may have a plurality of lattices 111a and a plurality of filling portions 111b for storing the coolant 120. The plurality of lattices 111a are formed by means of thermally bonding the outer synthetic resin film sheet 111 and an inner synthetic resin film sheet 112 thereof and the plurality of filling portions 111b are surrounded by the plurality of lattices 111a disposed thereon.

The flexible plated cooling pack 110 has a gap 111c for allowing the coolant 120 to flow and a flange portion 113 formed along the periphery portion thereof. The flange portion 113 is formed by means of thermally bonding the outer synthetic resin film sheet 111 and an inner synthetic resin film sheet 112 thereof.

The flange portion 113 may have one formed to be broader than the other so that it may allow the flexible plated cooling pack 110 to be more easily inserted between the crown portion 130 and the sweatband 170.

The tape-like flexible plated cooling pack 110 has a width of less than that of the sweatband 170 so that it may closely contact the crown portion 130 while being covered by the sweatband 170, and provides a cushioning effect at the forehead.

Meanwhile, the coolant 120 may be a phase change material (PCM) slurry.

The phase change material is defined as a latent heat storage material having a low melting point and a low vacuum change at phase change. The thermo-physical properties of the phase change material slurry, i.e., density, specific heat, thermal conductivity, and viscosity, were discussed for the temperature region of solid and liquid phases of the dispersion material (paraffin).

In order to satisfy such features, a paraffin series material among 200 types of phase change materials includes a slurry phase so that it may maintain a gel state still after phase change to always provide a cushioning effect.

Particularly, a common example thereof is RUBITHERM RT.

The RUBITHERM RT has merits such as an excellent heat storage capacity, a recycling possibility, a long life cycle, constant endothermic and exothermic reactions, a stable phase change cycle, environmental friendliness, and non-toxicity. In addition, during a phase change cycle, it has stable performance and good chemical stability and has a melting point at a temperature of −4° C. to 100° C. such that it is adaptable to a user's surrounding environment as shown in Table. 2

Table. 2 shows a performance of RUBITHERM RT

TABLE 2

| | | |
|---|---|---|
| Melting Point (approx) | ° C. | 28 |
| Congealing Point (PCM) | ° C. | 26 |
| Heat storage capacity Temperature range 19° C. to 35° C. | kJ/(kg) | 179 |
| Density solid at 15° C. | Kg/l | 0.87 |
| Density liquid at 70° C. | Kg/l | 0.75 |
| Volume expansion | % | 10 |
| Volume expansion r without phase change | 1/K | 0.001 |
| Specific heat capacity | kJ(kg · K) | 1.8/2.4 |
| Heat conductivity | W/(m · K) | 0.2 |
| Kin, Viscosity at 40° C. | mm$^2$/s | 4.5 |
| Flash Point(PCM) | ° C. | 164 |
| Corrosion | | Chemically inert with respect to most materials |
| Water hazard | | Water hazard class (WGK) 1 |

In addition, FIG. 3A and FIG. 3B illustrate the flexible plated cooling pack 110' having a shape corresponding to the plurality of pieces 131, 132, and 133 of the crown portion 130 (see FIG. 1)

As shown FIG. 3A and FIG. 3B, it may have a plurality of lattices 111'$a$ and a plurality of filling portions 111$b$' for storing the coolant 120'. The plurality of lattices 111$a$' are formed by means of thermally bonding the outer synthetic resin film sheet 111' and an inner synthetic resin film sheet 112' thereof and the plurality of filling portions 111$b$' are surrounded by the plurality of lattices 111$a$' disposed thereon.

The flexible plated cooling pack 110' has a gap 111$c$' for allowing the coolant 120' to flow and a flange portion 113' formed along the periphery portion thereof. The flange portion 113' is formed by means of thermally bonding the outer synthetic resin film sheet 111' and an inner synthetic resin film sheet 112' thereof.

The flange portion 113' may have a lower flange portion 113$a$' formed to be broader than other portions so that it may allow the flexible plated cooling pack 110' to be more easily inserted between the crown portion 130 and the sweatband 170.

Each flexible plated cooling pack 110' may be disposed to the inside of the plurality of pieces 131, 132, and 133 of the crown portion 130, and may be in close contact with the crown portion 130 by means of a strong static electric force because the second flexible plated cooling pack 110' is made of the synthetic resin film sheet 111 and the pieces 131, 132, and 133 are made of fabric.

Figure 4:
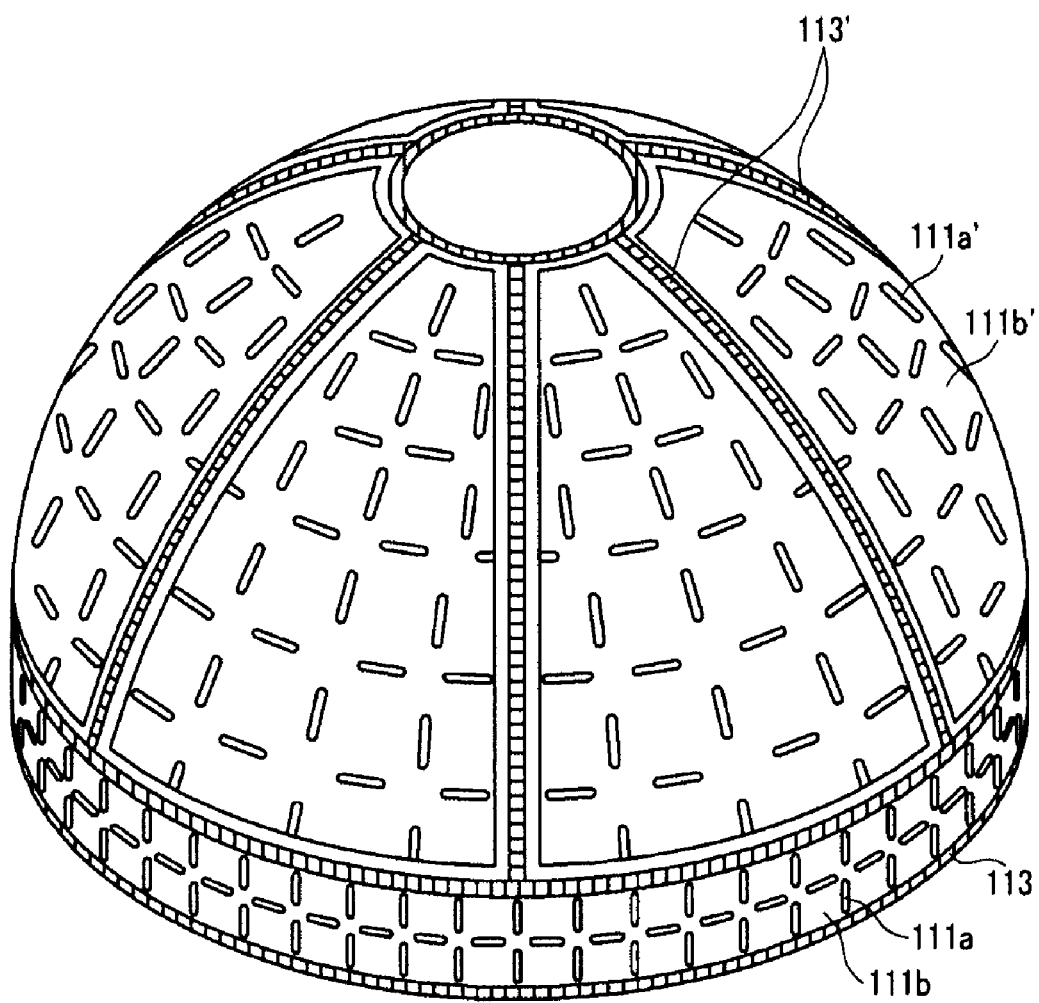
FIG. 4 is a perspective view showing how a plurality of flexible plated cooling packs are connected to each other according to an exemplary embodiment of the present invention.

FIG. 4 is a perspective view showing how a plurality of flexible plated cooling packs are connected to each other according to an exemplary embodiment of the present invention.

As shown in FIG. 4, the flange portions 113 of the flexible plated cooling pack 110 are overlapped with the flange portions 113' of the flexible plated cooling pack 110' so that a uniform shape corresponding to the crown portion 130 may be provided and thus a uniform cooling effect may be provided for the entire portion of the head.

Herein, a method for manufacturing a flexible plated cooling pack according to an exemplary embodiment of the present invention is described with reference to FIG. 5.

Figure 5:
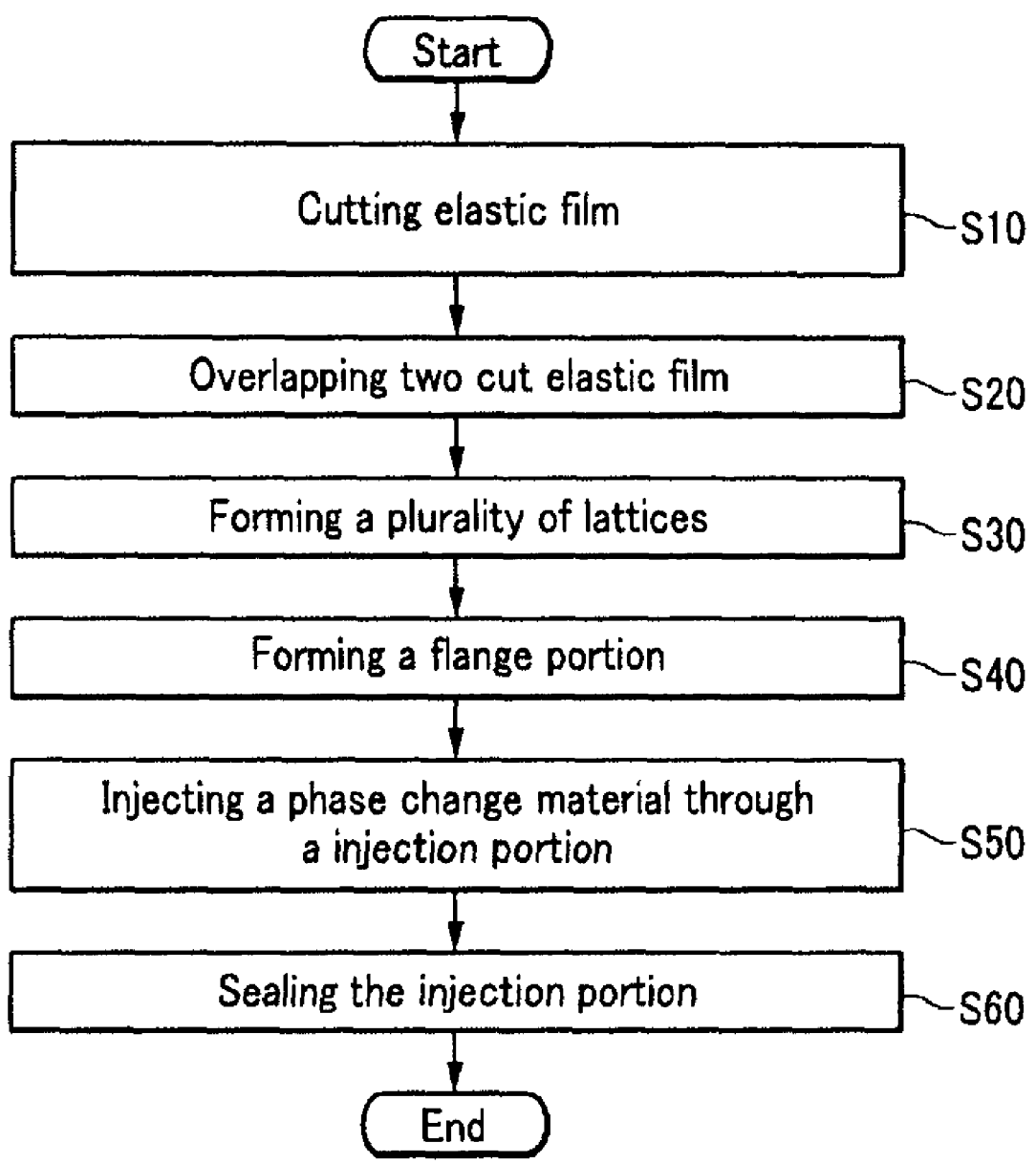
FIG. 5 is a flowchart showing how to manufacture a flexible plated cooling pack according to an exemplary embodiment of the present invention.

FIG. 5 is a flowchart showing how to manufacture a flexible plated cooling pack according to an exemplary embodiment of the present invention.

As shown in FIG. 5, in order to manufacture the flexible plated cooling pack 110 and 110', the synthetic resin film sheet 111 and 111' is cut from an elastic film into a shape corresponding to each of the pieces 131, 132, and 133 for forming the crown portion 130 or the sweatband 150 (S10).

As described above, the synthetic resin film sheet 111 and 111' may be made of a transparent and elastic film such as thermoplastic polyurethane film (TPU), so that it may be environmentally friendly, have good durability and elasticity, and may also have a freezing temperature of below −40° C. to provide a softer feel at sub-zero temperatures. In addition, it may have durability with respect to oil or fatty acids so that it may protect against leakage of the oil or fatty acids that is stored therein.

Two cut synthetic resin (elastic) film sheets 111 and 111' are then overlapped (S20).

When a hot bar or hot plate presses and heats the two overlapped synthetic resin film sheets 111 and 111', Lattices 111$a$ and 111$a$' are formed with gaps 111$c$ by means of thermally bonding (S30). At this time, it is preferable to use a high-frequency bonding as the thermal bonding such that only the corresponding bonding portions of the synthetic resin film sheets 111 and 111' are bonded. Accordingly, other parts of the elastic synthetic resin film sheets 111 may not be scorched and stick to each other.

The high-frequency bonding uses a frequency of 500 to 1600 kHz to form a high-frequency electro-magnetic field. Heat is generated due to an induced electricity loss to rapidly melt the material. The synthetic resin film sheets 111 and 111' may be easily and appropriately processed by the high frequency bonding.

The filling portions 111$b$ and 111$b$' surrounded by the lattices 111$a$ and 111$a$' are filled with the coolant that is injected though an injection portion 111$d$ and 111$d$'.

The periphery portion of the synthetic resin film sheet 111 and 111' having the filling portion 111$b$ and 111$b$' and the lattices 111$a$ and 111$a$' are sealed to form the flange portion 113 and 113' by the high frequency bonding except for the injection portion 111$d$ and 111$d$' associated with the gap 111$c$ and 111$c$' (S40).

The slurry-phase coolant 120 is injected though the injection portion 111$d$ and 111$d$' to the filling portions 111$b$ and 111$b$' of the flexible plated cooling pack 110 and 110' (S50).

When one filling portion 111$b$ and 111$b$' is filled with the coolant, another filling portion 111$b$ and 111$b$' is sequentially filled. Accordingly, the flexible plated cooling pack 110 may maintain a flat shape.

When the filling is completed, the injection portion 111d and 111d' is sealed with the high-frequency bonding (S60).

The cooling effect of the flexible plated cooling pack according to an exemplary embodiment of the present invention is described with reference to FIG. 6.

Figure 6:
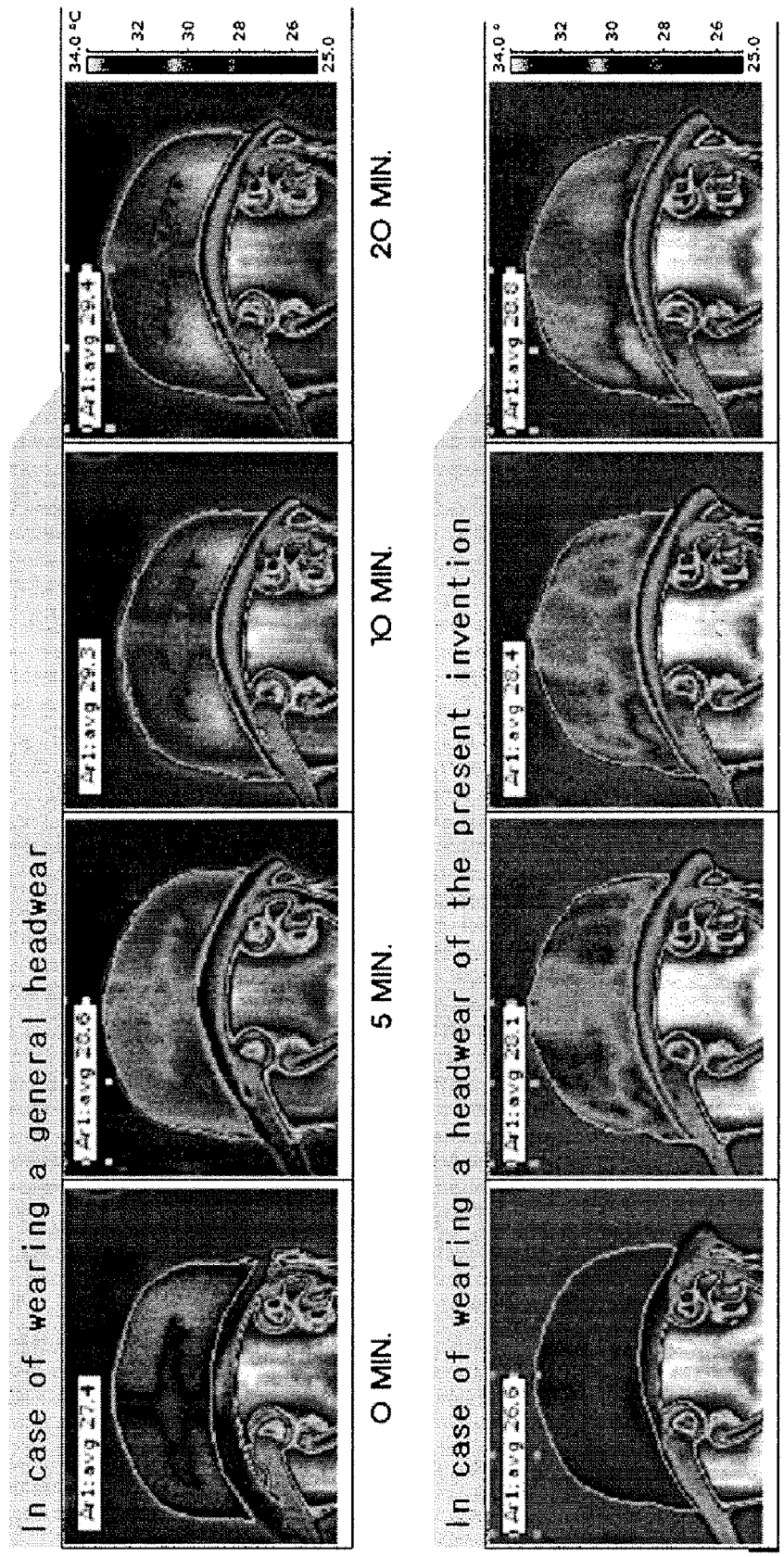
FIG. 6 shows a thermal image of a thermal mannequin according to an exemplary embodiment of the present invention.

FIG. 6 shows a thermal image of a thermal mannequin according to an exemplary embodiment of the present invention.

As shown in FIG. 6, the headwear using a flexible plated cooling pack according to an exemplary embodiment of the present invention may maintain a constant temperature at the periphery portion of the head for a long usage time, while the periphery temperature is increased when the conventional headwear is used for a long time.

Figure 7:
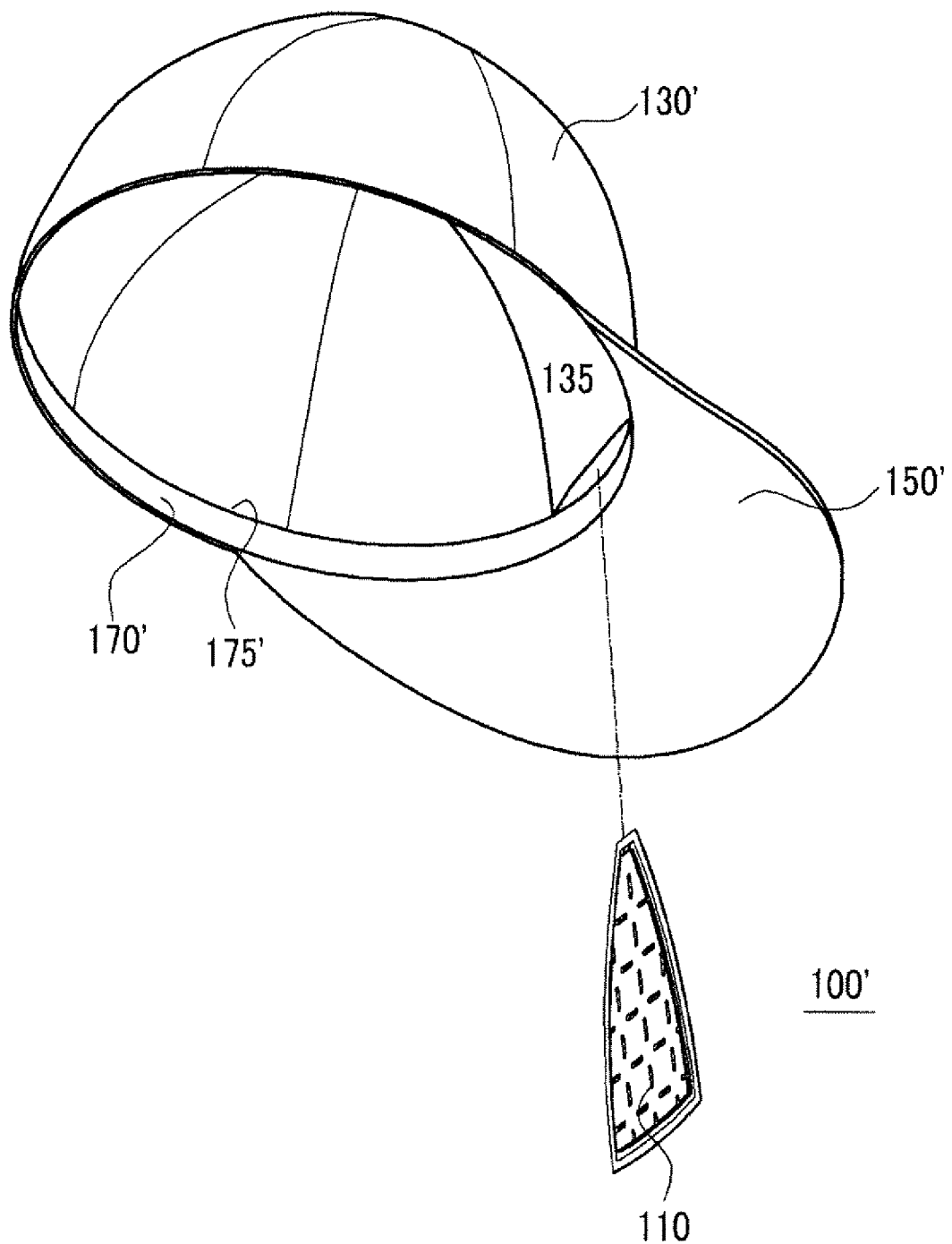
FIG. 7 is a perspective view of a flexible plated cooling pack in a state in which it is inserted into a pocket formed in each inner portion of a crown portion and a sweat band according to a second exemplary embodiment of the present invention.

Meanwhile, FIG. 7 is a perspective view of a flexible plated cooling pack in a state in which at least a portion thereof is inserted in a pocket formed at an inner portion of a crown portion and a sweat band according to another exemplary embodiment of the present invention.

As shown in FIG. 7, according to another exemplary embodiment of the present invention, headwear 100' may include a crown portion 130' that is placed on the head, a visor portion 150' protruding to shield sunlight at a part or the entirety of the lower portion of the crown portion 130', and a sweatband 170'.

The crown portion 130' and the sweatband 170' may have a pocket 135 and 175' at inner portion.

The pocket 135 and 175' may envelop the flexible plated cooling pack 110 and 110'.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A flexible plated cooling pack disposed at an inner portion of headwear having a crown portion that is placed on the head, a visor portion protruding outward from at least a part of the crown portion to shield sunlight, and a sweatband disposed according to a head circumferential direction at a lower portion of the crown portion, comprising an inner and outer synthetic resin film sheet bonded each other and a coolant filled therein, wherein the outer synthetic resin film sheet has a shape respectively corresponding to a piece of the crown portion and a sweatband and the coolant is always maintained in at least a gel state;
wherein the inner and outer synthetic resin film sheet is made of a transparent and elastic material.

2. The flexible plated cooling pack of claim 1, wherein a transparent and elastic material is selected from one of TPU, a polyethylene film, and a polyvinyl chloride film that is flexible at sub-zero temperatures.

3. A flexible plated cooling pack disposed at an inner portion of headwear having a crown portion that is placed on the head, a visor portion protruding outward from at least a part of the crown portion to shield sunlight, and a sweatband disposed according to a head circumferential direction at a lower portion of the crown portion, comprising an inner and outer synthetic resin film sheet bonded each other and a coolant filled therein, wherein the outer synthetic resin film sheet has a shape respectively corresponding to a piece of the crown portion and a sweatband and the coolant is always maintained in at least a gel state;
wherein the flexible plated cooling pack includes a plurality of lattices formed on the inner and outer synthetic resin film sheets, a filling portion surrounded by the lattice, a gap disposed between the plurality of lattices, and a flange portion integrated at an periphery portion thereof.

4. The flexible plated cooling pack of claim 3, wherein the lattices and the flange portion is formed on the inner and outer synthetic resin film sheets by high frequency bonding.

5. The flexible plated cooling pack of claim 3, wherein the filling portion is filled with a coolant which is slurry dispersed with a paraffin series phase change material.

6. The flexible plated cooling pack of claim 3, wherein the lattices and the gaps prevents a volume of the flexible plated synthetic resin cooling pack from be partially increased at the phase change.

7. The flexible plated cooling pack of claim 5, wherein the slurry contains RUBITHERM RT having a stable phase change cycle and that is appropriate for a small volume and low temperature variance.

8. A method for making a flexible plated cooling pack for headwear, comprising:
cutting an elastic synthetic resin film sheet in correspondence with a shape of each piece of a crown portion and a sweatband of headwear;
overlapping at least two cut elastic synthetic resin film sheets;
forming a plurality of lattices on the overlapped cut elastic synthetic resin film sheets with a predetermined gap;
forming a flange portion at an periphery portion of the overlapped cut elastic synthetic resin film sheet except for an injection portion by means of thermal bonding;
charging a coolant maintaining at least a gel state through the injection portion connected to the gap between the plurality of lattices to form a filling portion with a constant thickness; and
sealing the injection portion.

9. The method for making a flexible plated cooling pack for headwear of claim 8, wherein the forming of the flange portion and the lattices, and the sealing of the injection portion are performed by high frequency bonding.

10. A flexible plated cooling pack inserted in a pocket formed at an inner portion of headwear having a crown portion that is placed on the head, a visor portion protruding outward from at least a part of the crown portion to shield sunlight, and a sweatband disposed according to a head circumferential direction at a lower portion of the crown portion, comprising an inner and outer synthetic resin film sheet bonded each other and a coolant filled therein, wherein the outer synthetic resin film sheet has a shape respectively corresponding to a piece of the crown portion and a sweatband and the coolant is always maintained in at least a gel state;
wherein the inner and outer synthetic resin film sheet is made of a transparent and elastic material.

11. The flexible plated cooling pack of claim 10, wherein a transparent and elastic material is selected from one of TPU, a polyethylene film, and a polyvinyl chloride film that is flexible at sub-zero temperatures.

12. A flexible plated cooling pack inserted in a pocket formed at an inner portion of headwear having a crown portion that is placed on the head, a visor portion protruding outward from at least a part of the crown portion to shield sunlight, and a sweatband disposed according to a head circumferential direction at a lower portion of the crown portion, comprising an inner and outer synthetic resin film sheet bonded each other and a coolant filled therein, wherein the outer synthetic resin film sheet has a shape respectively corresponding to a piece of the crown portion and a sweatband and the coolant is always maintained in at least a gel state;

wherein the flexible plated cooling pack includes a plurality of lattices formed on the inner and outer synthetic resin film sheets, a filling portion surrounded by the lattice, a gap disposed between the plurality of lattices, and a flange portion integrated at an periphery portion thereof.

13. The flexible plated cooling pack of claim 12, wherein the lattices and the flange portion is formed on the inner and outer synthetic resin film sheets by high frequency bonding.

14. The flexible plated cooling pack of claim 12, wherein the filling portion is filled with a coolant which is slurry dispersed with a paraffin series phase change material.

15. The flexible plated cooling pack of claim 14, wherein the slurry contains RUBITHERM RT having a stable phase change cycle and that is appropriate for a small volume and low temperature variance.

16. The flexible plated cooling pack of claim 12, wherein the lattices and the gaps prevents a volume of the flexible plated synthetic resin cooling pack from be partially increased at the phase change.

* * * * *